United States Patent [19]

Föster et al.

[11] Patent Number: 4,976,928
[45] Date of Patent: Dec. 11, 1990

[54] DEVICE FOR PERFORMING EXOTHERMIC CATALYTIC GAS REACTIONS FOR THE SYNTHESIS OF AMMONIA OR METHANOL

[76] Inventors: Friedrich Föster, Rauschenburgstr. 1; Hans-Gunter Brieke, Godekinstr. 55, both of 4600 Dortmund 30; Hans-Dieter Marsch, Overhoffstr. 193, 4600 Dortmund 76, all of Fed. Rep. of Germany

[21] Appl. No.: 946,162

[22] Filed: Dec. 23, 1986

Related U.S. Application Data

[63] Continuation of Ser. No. 672,713, Nov. 19, 1984, abandoned.

[30] Foreign Application Priority Data

Nov. 29, 1983 [DE] Fed. Rep. of Germany ....... 3343114

[51] Int. Cl.$^5$ ............................................. C10C 1/00
[52] U.S. Cl. .................... 422/148; 422/191; 422/192; 422/194; 422/195; 422/207; 422/218
[58] Field of Search ............... 422/148, 191, 192, 194, 422/195, 207, 218; 423/360, 361

[56] References Cited

U.S. PATENT DOCUMENTS

| | | | |
|---|---|---|---|
| 3,442,626 | 5/1969 | Browne | 423/361 |
| 3,663,179 | 5/1972 | Mehta et al. | 422/148 |
| 3,694,169 | 9/1972 | Fawcett et al. | 422/148 |
| 4,372,920 | 2/1983 | Zardi | 422/148 |
| 4,405,562 | 9/1983 | Zardi et al. | 422/148 |

*Primary Examiner*—Robert J. Warden
*Assistant Examiner*—Timothy M. McMahon
*Attorney, Agent, or Firm*—Marshall & Melhorn

[57] ABSTRACT

The invention relates to a device for performing exothermic catalytic gas reactions for synthesis of ammonia or methanol, comprising essentially a high-pressure shell, an insert, and an upper cover, the insert being equipped at least with two superimposed annular cylindrical catalyst containments having a gas-permeable inner and outer wall for radial gas flow from the outside towards the inside and with two tubular gas/gas heat exchangers arranged centrally in the first and second catalyst containers.

6 Claims, 1 Drawing Sheet

DEVICE FOR PERFORMING EXOTHERMIC CATALYTIC GAS REACTIONS FOR THE SYNTHESIS OF AMMONIA OR METHANOL

This case is a continuation of U.S. Ser. No. 06/672,713 filed on Nov. 19, 1984 and now abandoned.

BACKGROUND OF THE INVENTION

The invention relates to a device for performing exothermic catalytic gas reactions for the synthesis of ammonia or methanol. The device is comprised essentially of a high-pressure shell; an upper cover; and an insert with at least two superimposed annular cylindrical catalyst containers each having a gas-permeable inner and outer wall to provide for the radial flow of gas from the outside towards the inside and with two tubular gas/gas heat exchangers arranged centrally relative to the first and second catalyst containers.

The catalytic high-pressure synthesis for producing ammonia and methanol is an exothermic process. To obtain an optimum reaction, i.e. an optimum conversion yield, it is critical that the process be conducted in an ideal temperature range. The most favorable reaction temperatures can be maintained by cooling the gases heated during the reaction through indirect heat exchange with freshly introduced gas. As the fresh gas must be delivered to the first catalyst bed at a temperature of above 300° C., the fresh gas will best be heated by hot reaction gas in indirect heat exchange.

Cooling of the reaction gas may be accomplished either by providing for the reaction to take place at an almost constant temperature, as this is practiced in catalyst tube furnaces or full-space furnaces with cooling coils in the catalyst mass, or by reducing the temperatures stepwise at the outlets of the individual catalyst beds of the entire catalyst mass.

Numerous devices, i.e. furnaces, are known to be used for fulfilling the above requirements. It is known, for instance, to arrange the catalyst mass in several superimposed beds with tubular heat exchangers installed between the beds for heating the fresh gas and for reducing the reaction temperatures.

Referring to German patent application No. DE-OS 30 26 199, an axial/radial flow reactor with centrally arranged heat exchangers is shown. In this reactor, the cold fresh gas flows upwards through the tubes of the individual heat exchangers, while the hot reaction gas flows on the shellside. Each heat exchanger is arranged centrally in the lower part of the annular catalyst basket. Catalyst basket and heat exchanger are installed in such a way that the heat exchanger can only be dismantled after the catalyst basket has been emptied and removed. Furthermore, an elastic link has to be provided between the individual heat exchangers which must first be loosened to avoid damage before one is able to dismantle the heat exchanger. In replacing the catalyst, it is not possible to remove the catalyst basket downward in the reactor. The fact that, prior to dismantling a heat exchanger, the catalyst basket has first to be removed is reason for having to design the upper cover extending over the entire cross-section of the high-pressure shell. A cover of reduced diameter cannot be used.

Other known types of furnaces with heat exchangers integrated in the catalyst beds generally have the disadvantage that they require components which are complicated and difficult to replace and that they encounter sealing problems due to the high temperature and pressure differences generated during operation of an ammonia or methanol synthesis plant.

SUMMARY OF THE INVENTION

The object of the present invention is to produce a reactor design which eliminates the disadvantages encountered in the types of reactors previously known. According to the present invention the objectives are typically achieved with a device for performing exothermic catalytic gas reactions for the synthesis of ammonia or methanol comprising essentially of high-pressure shell, an insert, and an upper cover, the insert being equipped at least with two superimposed annular cylindrical catalyst containments having a gas-permeable inner and outer wall for radial gas flow from the outside towards the inside and with two tubular gas/gas heat exchangers arranged centrally in the first and second catalyst containers.

A further embodiment of this invention provides for the central guide tube being surrounded by the annular make-up gas bypass line.

The invention yields on the one hand an optimum heat exchange in the ammonia converter as the heat exchangers have been designed for an optimum diameter/length ratio in line with the prevailing gas volumes and the required gas velocities, and entails, on the other hand, a simplification both as regards the integration of heat exchangers in catalyst beds and the operation of the reactor insert or of the heat exchangers.

The manner in which the heat exchangers are medially disposed in an area of reduced diameter within the reactor permits the heat exchangers and catalyst beds to be individual units which can be installed and dismantled separately. A reactor designed after this fashion requires no complicated catalyst filling and emptying facilities as the beds can be serviced after removing them from the reactor. Likewise, should the need arise to service the heat exchanges, they may be removed by themselves.

The arrangement of the heat exchangers centrally in the catalyst bed, as featured in the present invention, allows the heat exchangers to be designed for optimum dimensions, i.e. best heat transfer coefficients and most economical tube dimensions. The heat exchanger diameter is no longer necessarily dependent upon the reactor diameter. As is known in heat exchanger practice, certain relations between gas velocities in the tubes and gap widths between the tubes have to be considered for obtaining an optimum heat exchange.

Furthermore, a device embodying the features of this invention allows heat exchangers of optimum dimensions to be installed centrally in the catalyst containers of reactors of 2 meters or more in diameter without having to encounter the difficulties mentioned above. The upper opening can be reduced to a diameter which allows use of an easily operable conventional cover. The periods of installation which are thereby shortened ensure optimum operating times.

BRIEF DESCRIPTION OF THE DRAWING

The above objects and advantages of the invention will be more clearly understood by one skilled in the art from reading the following detailed description of an embodiment of the invention when considered in the light of the accompanying drawing, in which.

DETAILED DESCRIPTION OF PREFERRED EMBODIMENT

Figure 1:
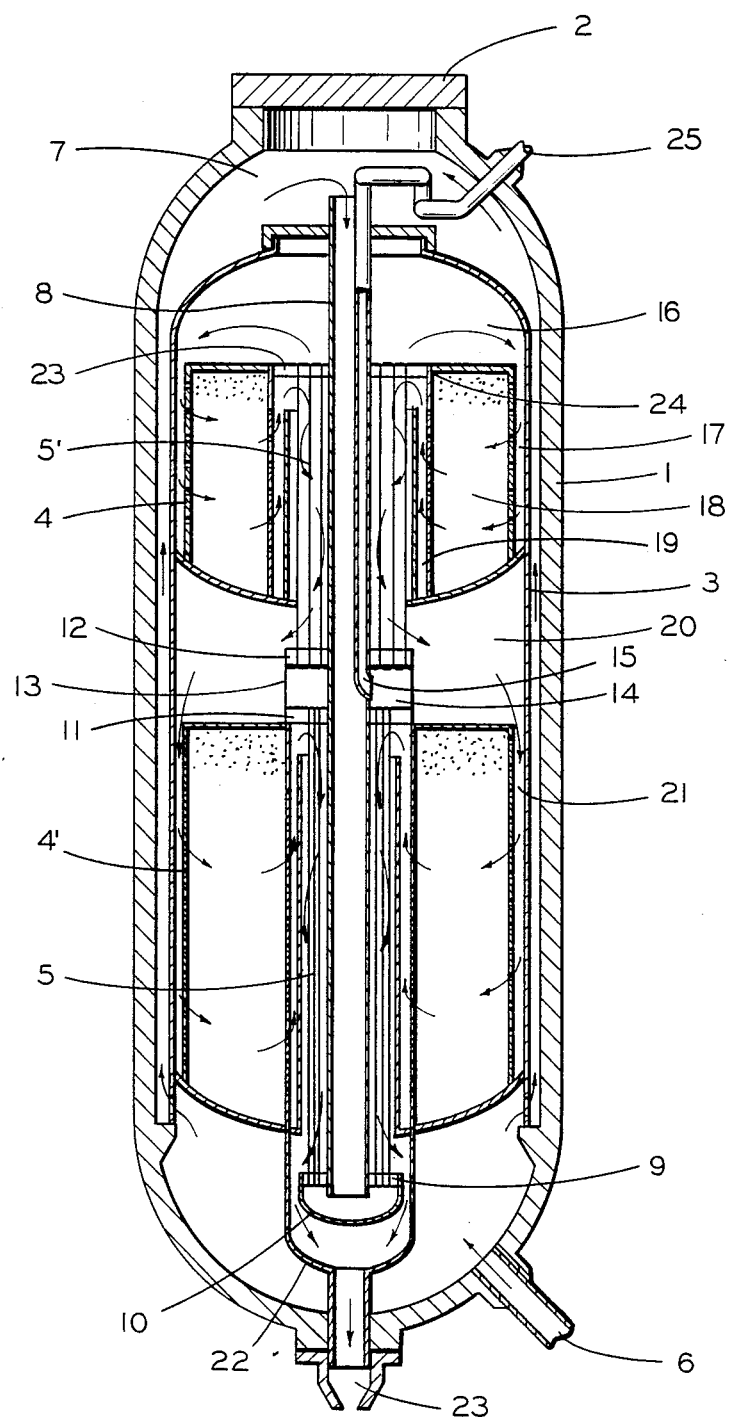
FIG. 1 is a cross-sectional view of a reactor embodying the features of the invention.

A device is illustrated in FIG. 1 for performing exothermic catalytic gas reactions for the synthesis of ammonia or methanol and comprises essentially a high-pressure shell 1, an upper cover 2, and an insert 3 equipped with the catalyst containers 4, 4' and the gas/gas heat exchangers 5, 5'. The description of the gas flow during operation of the device and an explanative of the structural interconnection of the individual components is also shown.

The recycle gas, called fresh gas for the purpose of this description, enters at a low temperature through a gas inlet nozzle 6 into a high-pressure shell 1 and thence travels upwards in the annular space between the high-pressure shell 1 and the insert 3. On its way through this annular space, the fresh gas cools the high-pressure shell 1 from the inside. After having reached a zone 7 above the insert 3, the fresh gas flows downward through a central guide tube 8 and accumulates just in front of a tubesheet 9 of the first gas/gas heat exchanger 5. A bonnet 10 is provided for at the lower portion of the tubesheet 9 of the gas/gas heat exchanger 5 and directs the fresh gas to be heated into the tubes of the gas/gas heat exchanger 5. This first gas/gas heat exchanger 5 extends centrally over the full length of the container 4' for the second catalyst bed. The upper portion 11 of the tubesheet, the lower portion 12 of the tubesheet of the second gas/gas heat exchanger 5' in the container 4 for the first catalyst bed, and the shell plate 13 form a chamber 14 provided for the temperature control of the partially heated fresh gas.

The chamber 14 is connected to a bypass line 15 through which cold fresh gas may be admixed with the partially heated fresh gas. From chamber 14, the partially heated fresh gas passes through the tubes of the second gas/gas heat exchanger 5' then exits to the zone 16 above the container 4 for the first catalyst bed. This zone has a connection to a cold-gas line (not shown) through which cold gas may be admixed, if required, for lowering the temperature of the heated fresh gas leaving the second gas/gas heat exchanger. After temperature adjustment, the fresh gas leaving the free space 16 undergoes a change in direction and flows downwardly into an annular space 17 disposed between the insert 3 and the perforated outer wall of the catalyst container 4. The gas then spreads over the first catalyst bed 18, flows radially toward an annular space 19, rises, and finally reaches the shell space of the second gas/gas heat exchanger 5'. The recycle gas heated in the first catalyst bed due to the exothermic reaction and thereby changing into reaction gas enters into indirect heat exchange with the fresh gas to be heated which flows through the tubes of the gas/gas heat exchanger 5'.

After passing through the heat exchanger, the gas stream reaches the zone between the first and second catalyst beds 20, subsequently entering the annular space 21 between the insert 3 and the perforated outer wall of the catalyst container 4'. The penetration of the second catalyst bed and of the shell space of the first gas/gas heat exchanger 5 takes place as described for the first catalyst bed and the second gas/gas heat exchanger 5'. The partially cooled reaction gas stream from the shell space of the first gas/gas heat exchanger 5 is collected by means of bed 22 before leaving the high-pressure shell via nozzle 26.

The two gas/gas heat exchangers 5, 5' are firmly connected, i.e. welded, to the guide tube 8 and are adapted to rest on the upper rim of the inner wall of the lower catalyst container 4'. From this point both heat exchangers may freely expand unilaterally without suffering detrimental thermal expansion. Sealing of the upper portion 23 of the tubesheet of the second heat exchanger 5' and of the guide tube 8 on the cover of the first catalyst container 4 or on the cover of the insert is effected: by means of a conventional stuffing box packing 24.

An essential feature of the invention is that both heat exchangers 5, 5' and the guide tube 8 form a firm unit and that the fixed point of the unit is near the middle of the unit so that the hot part of both heat exchangers may expand freely.

What is claimed is:

1. A device for performing exothermic catalytic gas reactions for the synthesis of ammonia or methanol, including a high-pressure shell and an insert inside the shell, the insert having at least two superimposed annular cylindrical catalyst containers including gas-permeable inner and outer walls for the radial flow of gas from the outside towards the inside and at least two tubular gas/gas heat exchangers arranged centrally in the catalyst containers, comprising:

(a) a central guide tube extending from a zone above the insert to which said tube is sealed to a point below a lower end of a first one of the gas/gas heat exchangers;

(b) a bonnet disposed beneath said lower end of said first gas/gas heat exchanger serving as a baffle means for directing gas introduced down said guide tube up through said first gas/gas heat exchanger;

(c) a first tube bundle of said first gas/gas heat exchanger installed in a first shell shorter than said tube bundle so as to allow gas to enter and leave at both ends of said first shell, said first tube bundle and said first shell surrounding a lower end of said guide tube and extending through a second one of the catalyst containers, and an upper portion of a tubesheet of said first gas/gas heat exchanger having a gastight and firm connection around said guide tube and a gastight support on an upper rim of the inner wall of said second catalyst container;

(d) a second tube bundle of a second one of the gas/gas heat exchangers installed in a second shell shorter than said second tube bundle so as to allow gas to enter and leave at both ends of said second shell, said second tube bundle and said second shell surrounding an upper end of said guide tube and extending through a first one of the catalyst containers, a lower portion of a tubesheet of said second gas/gas heat exchanger having a gastight and firm connection around said guide tube, and an upper portion of said tubesheet being movably sealed against a cover of said first catalyst container; and (e) a chamber defined between said upper portion of said tubesheet of said first gas/gas heat exchanger and said lower portion of said tubesheet of said second gas/gas heat exchanger and in communication with said first and second tube bundles whereby gas directed by said bonnet flows upwardly through said first tube bundle, said chamber and said second tube bundle and then flows downwardly through said first catalyst container, between said second shell and said second tube bundle, through said second catalyst container, and then between said first shell and said first tube bundle, and said first and second gas/gas heat exchangers and said central guide tube connected together to form a unit removably supported by said second catalyst container and detachable from the insert.

2. The invention defined in claim 1 wherein the high-pressure shell includes an inlet connected between a source of gas to be cycled and an annular space between the high-pressure shell and the insert and wherein an upper end of said guide tube is open to said annular space.

3. The invention defined in claim 1 wherein a by-pass line is connected between said chamber and a source of gas at a lower temperature than gas passing through said chamber from said first tube bundle to said second tube bundle.

4. The invention defined in claim 1 wherein the insert has a nozzle extending through a wall of the high-pressure shell for directing reaction gas exiting from between said first shell and said first tube bundle.

5. The invention defined in claim 1 wherein the high-pressure shell includes an aperture and a cover for closing said aperture and wherein said guide tube and said first and second gas/gas heat exchangers are removable as a unit from the high-pressure shell through said aperture.

6. In a device for performing exothermic catalytic gas reactions for the synthesis of ammonia or methanol, including a high-pressure shell and an insert inside the shell, the insert having at least two superimposed annular cylindrical catalyst containers including gas-permeable inner and outer walls for the radial flow of gas from the outside towards the inside and at least two tubular gas/gas heat exchangers arranged centrally in the catalyst containers, the improvement comprising:

a central guide tube extending from a zone above the insert through the gas/gas heat exchangers to a point below a lower end of a first one of the heat exchangers;

a bonnet disposed beneath said lower end of said first heat exchanger serving as a baffle means for directing gas introduced down said guide tube up through said first heat exchanger;

a first tube bundle of said first heat exchanger surrounding a lower end of said guide tube and extending through a second one of the catalyst containers, and an upper portion of a tubesheet of said first heat exchanger having a gastight and firm connection around said guide tube and being removably supported in a gastight relationship by the inner wall of said second catalyst container;

a second tube bundle of a second one of the heat exchangers surrounding an upper end of said guide tube and extending through a first one of the catalyst containers, a lower portion of a tubesheet of said second heat exchanger having a gastight and firm connection around said guide tube, and an upper portion of said tubesheet being movably sealed against said first catalyst container; and a chamber defined between said upper portion of said tubesheet of said first heat exchanger and said lower portion of said tubesheet of said second heat exchanger and in fluid communication with said first and second tube bundles whereby said central guide tube, said bonnet, said first and second heat exchangers and said chamber form a unit removably supported by said second catalyst container and detachable from the insert.

* * * * *